United States Patent
Sevenler et al.

(10) Patent No.: US 11,561,221 B2
(45) Date of Patent: *Jan. 24, 2023

(54) DYNAMIC TRACKING OF CAPTURED TARGETS FOR ENHANCED DIGITAL BIOSENSING

(71) Applicant: Trustees of Boston University, Boston, MA (US)

(72) Inventors: Derin Sevenler, Boston, MA (US); M. Selim Ünlü, Newton Highlands, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 614 days.

This patent is subject to a terminal disclaimer.

(21) Appl. No.: 16/401,963

(22) Filed: May 2, 2019

(65) Prior Publication Data

US 2019/0339268 A1 Nov. 7, 2019

Related U.S. Application Data

(60) Provisional application No. 62/665,678, filed on May 2, 2018.

(51) Int. Cl.
*G01N 33/569* (2006.01)
*G06T 7/00* (2017.01)

(52) U.S. Cl.
CPC ......... *G01N 33/569* (2013.01); *G06T 7/0012* (2013.01)

(58) Field of Classification Search
None
See application file for complete search history.

(56) References Cited

U.S. PATENT DOCUMENTS

| | | | | |
|---|---|---|---|---|
| 2003/0096302 A1* | 5/2003 | Yguerabide | ............ | G01N 21/47 435/7.1 |
| 2006/0240416 A1* | 10/2006 | Banerjee | .............. | C12Q 1/6876 435/7.1 |
| 2011/0059467 A1* | 3/2011 | Ting | ........................ | B82Y 15/00 252/301.36 |
| 2012/0220494 A1* | 8/2012 | Samuels | ............ | C12N 15/1075 506/26 |
| 2014/0255939 A1* | 9/2014 | Wong | .................... | C12Q 1/6813 536/23.1 |
| 2018/0023124 A1* | 1/2018 | Collins | ................ | C12Q 1/6827 435/6.11 |
| 2018/0275097 A1* | 9/2018 | San | .................. | G01N 27/44721 |
| 2019/0048415 A1* | 2/2019 | Walter | ................. | C12Q 1/6834 |
| 2021/0048435 A1* | 2/2021 | Alexander | ....... | G01N 33/54346 |
| 2021/0318309 A1* | 10/2021 | Groves | ................ | G01N 15/147 |

OTHER PUBLICATIONS

Alix-Panabieres et al., "Clinical Applications of Circulating Tumor Cells and Circulating Tumor DNA as Liquid Biopsy", Cancer Discovery, 6, 479-491, (2016).
Alsdurf et al., "The cascade of care and diagnosis and treatment of latent tuberculosis infection: a systematic review and meta-analysis", The Lancet Infectious Diseases, 16, (11.), 1269-1278, (2016).
Antoine et al., "Mechanistic Biomarkers Provide Early and Sensitive Detection of Acetaminophen-Induced Acute Live Injury at First Presentation to Hospital", Hepatology, 58, (2.), 777-787, (2013).
Baaske et al., "Single-molecule acid interactions monitored on a label-free microactivity biosensor platform", Nature Nanotechnology, 9, (11.), 933-939, (2014).
Besteman et al., "Enzyme-Coated Carbon Nanotubes as Single-Molecule Biosensors", Nano Letters, 3, (6.), 727-730, (2003).
Cohen JD et al., "Combined circulating tumor DNA and protein biomarker-based liquid biopsy for the earlier detection of pancreatic cancers", PNAS, 114, (38.), 10202-10207, (2017).
Cohen L et al., "Digital direct detection of microRNAs using single molecule arrays", Nucleic Acids Research, 45, (14.), 1-9, (2017).
Hill et al., "The bio-barcode assay for the detection of protein and nucleic acid targets using DTT-induced ligand exchange", Nature Protocols, 1, (1.), 324-336, (2006).
Papa et al., "Time Course and Diagnostic Accuracy of Glial and Neuronal Blood Biomarkers GFAP and UCH-L1 in a Large Cohort of Trauma Patients With and Without Mild Traumatic Brain Injury", JAMA Neurology, 73, (5.), 551-560, (2016).
Rissin et al., "Polymerase-free measurement of microRNa-122 with single base specificity using single molecule arrays: Detection of drug-induced liver injury", Plos One, 12, (7.), 1-15, (2017).
Schoepp et al., "Rapid pathogen-specific phenotypic antibiotic susceptibility testing using digital LAMP quantification in clinical samples", Science Translational Medicine, 9, (410.), 1-12, (2017).
Sevenler et al., "Digital Microarrays: Single-Molecule Readout with Interferometric Detection of Plasmonic Nanorod Labels", ACS Nano, 12, (6.), 5880-5887, (2018).
Shurtleff et al., "Pre-symptomatic diagnosis and treatment of filovirus diseases", Frontiers in Microbiology, 6, 1-13, (2015).
Sorgenfrei et al., "Label-free single-molecule detection of DNA-hybridization kinetics with a carbon nanotube field-effect transistor", Nature Nanotechnolgy, 6, (2.), 126-132, (2011).

(Continued)

*Primary Examiner* — Ann Montgomery
(74) *Attorney, Agent, or Firm* — Nixon Peabody LLP; Ronald I. Eisenstein; David F. Crosby

(57) ABSTRACT

Herein is described kinetic assay, in which individual binding events are detected and monitored during sample incubation. This method uses interferometric reflectance imaging to detect thousands of individual binding events across a multiplex solid phase sensor with a large area. A dynamic tracking procedure is used to measure the duration of each event. From this, the total rates of binding and de-binding as well as the distribution of binding event durations are determined. Systems and components for performing the kinetic assay are also described.

12 Claims, 10 Drawing Sheets

(10 of 10 Drawing Sheet(s) Filed in Color)

(56) References Cited

OTHER PUBLICATIONS

Squires et al., "Making it stick: convection, reaction and diffusion in surface-based biosensors", Nature Biotechnology, 26, (4.), 417-426, (2008).
Vogelstein et al., "Digital PCR", PNAS, 96, (16.), 9236-9241, (1999).
Walt, "Optical Methods for single Molecule Detection and Analysis", Analytical Chemistry, 85, (3.), 1258-1263, (2012).
Wu et al., "Incorporation of Slow Off-Rate Modified Aptamers Reagents in Single Molecule Array Assays for Cytokine Detection with Ultrahigh Sensitivity", Analytical Chemistry, 88, (17.), 8385-8389, (2016).

* cited by examiner

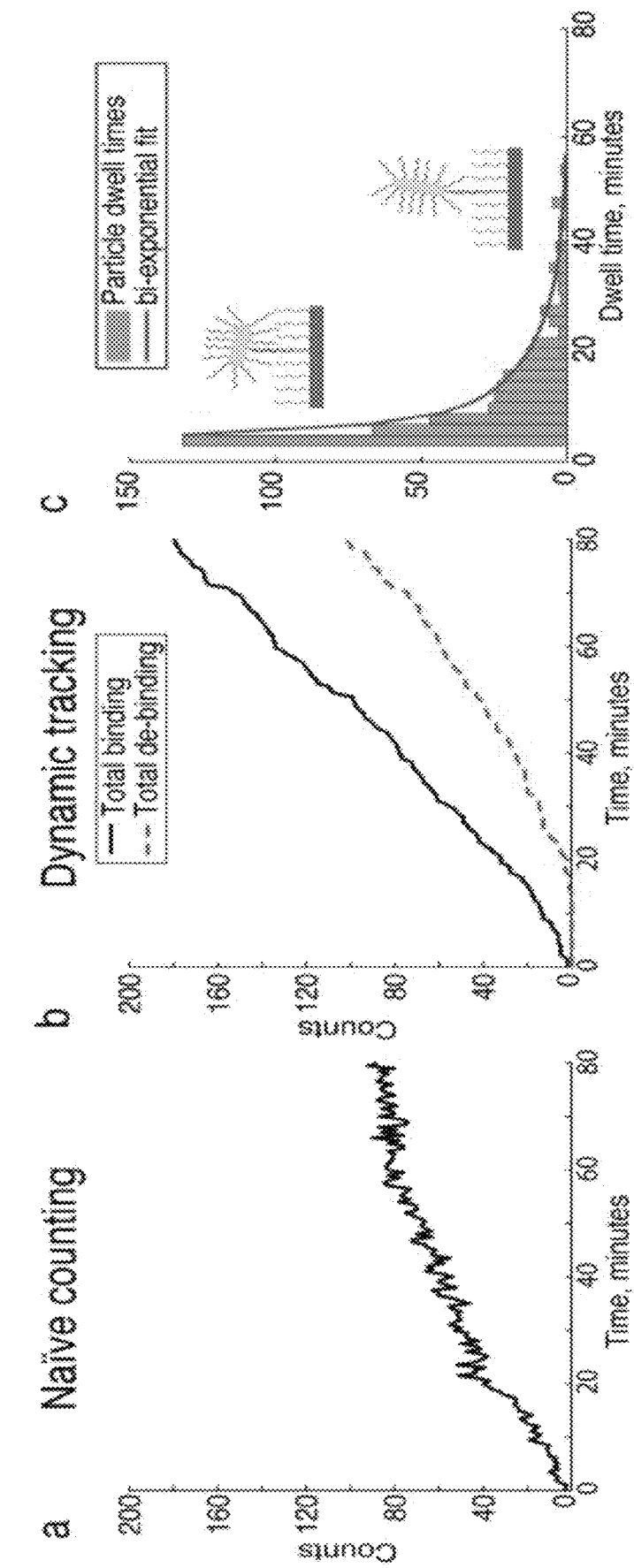

DYNAMIC TRACKING OF CAPTURED TARGETS FOR ENHANCED DIGITAL BIOSENSING

CROSS-REFERENCE TO RELATED APPLICATIONS

This application claims any and all benefits as provided by law including benefit under 35 U.S.C. § 119(e) of the U.S. Provisional Application No. 62/665,678, filed May 2, 2018, the contents of which are incorporated herein by reference in its entirety

GOVERNMENT SUPPORT

This invention was made with Government Support under Contract No. R21AI113715 awarded by the National Institutes of Health. The Government has certain rights in the invention.

FIELD OF THE INVENTION

This invention relates to systems, methods and assays for measuring single particles. More specifically, to the measurement of particles transiently captured by capture agents.

BACKGROUND

Several of the promises of precision medicine rely on ultra-sensitive molecular diagnostic technologies. Liquid biopsies of circulating genomic, transcriptomic, or proteomic biomarkers of cancer promise earlier detection and treatment, as well as improved guidance of targeted therapies in treating minimum residual disease (Cohen J D, et al. (2017), *PNAS* 114(38):10202-10207; Alix-Panabières C et al., (2016), *Cancer Discov.* doi:10.1158/2159-8290.CD-15-1483). Similarly, sensitive and specific molecular diagnostic tests for infectious pathogens are vital for the identification and management of pre- or asymptomatic individuals (Shurtleff A C et al. W (2015), *Front Microbiol* 6. doi: 10.3389/fmicb.2015.00108; Alsdurf H et al. (2016), *The Lancet Infectious Diseases* 16(11):1269-1278). Likewise, panel assays of circulating biomarkers could soon improve the accuracy of diagnosis of injuries such as acute liver failure or traumatic brain injury (Antoine D J, et al. (2013), *Hepatology* 58(2):777-787; Papa L, et al. (2016), *JAMA Neurol* 73(5):551-560).

These pressing clinical needs have motivated the development of a variety of ultra-sensitive assay technologies, culminating in technologies capable of single molecule detection. A unifying characteristic of essentially all of these assay technologies is that they employ molecular recognition agents (or 'capture probes') such as antibodies, nanobodies, peptides, oligonucleotides, aptamers, or other agents that bind specifically to the molecule of interest. Single molecule detection technologies commonly then use droplet emulsions (Vogelstein B, Kinzler K W (1999), *PNAS* 96(16): 9236-9241) or microwell arrays (Cohen L, Walt D R (2017), *Annual Review of Analytical Chemistry* 10(1):345-363) to isolate and then enumerate the precise number of analyte molecules bound to the capture probes.

In terms of signal transduction, it is clear that single molecule detection is 'as good as it gets' (Walt D R (2012), *Anal Chem* 85(3):1258-1263). But, transducing the amount of captured analyte is only one half of the picture—the analyte must be captured in the first place. Even with single molecule detection, assay performance is still limited by the affinity of the capture probes. This causes sensitivity and specificity to vary widely between different probe-analyte pairs. For example, it is now relatively routine to quantify some molecular species (e.g. genomic DNA) with single-copy sensitivity and precision (Schoepp N G et al. (2017), *Science Translational Medicine* 9(410):eaa13693) while the detection limits of other analytes (e.g. microRNA) are many orders of magnitude worse (Rissin D M et al. (2017), *PLOS ONE* 12(7):e017966; Cohen L, et al. (2017), *Nucleic Acids Res* 45(14):e137-e137; Wu D et al., (2016), *Anal Chem* 88(17):8385-8389). Probe affinity can also vary between samples. Variations in extensive properties of the sample such as pH and ion content change the free energy of binding, and variable amounts of nonspecific background binding further complicates quantitation.

Current leading single molecule detection technologies rely on signal amplification reactions. These are endpoint assays: the probe molecules are incubated with the sample for a set amount of time, after which the reaction is halted so that amplification and detection can be performed. What is measured is the amount of bound analyte at the instant the incubation is halted.

A recent development in single particle detection is the development of a 'digital microarray' assay technology which rapidly enumerates individual captured molecules across hundreds of microarray spots (Sevenler D et al., (2018), *ACS Nano* 12(6):5880-5887). This technology uses probe-conjugated gold nanorods as molecular labels, and an interferometric reflectance imaging sensor (IRIS) to rapidly detect individual nanorods with a low-magnification (10×-20×) objective. The large field of view enabled a similar throughput to commercial fluorescence readers while enhancing the limit of detection and dynamic range by a factor of approximately 10,000. The assay reaction is based on the bio-barcode assay developed by others (Hill H D et al., (2006), *Nat Protoc* 1(1):324-336) and is compatible with a range of different analytes.

In contrast to endpoint assays, kinetic assays directly measure probe-analyte interactions during course of the incubation. Kinetic assays collect more information than endpoint assays: they can measure not just concentration but also molecular affinity via rates of association and dissociation. This could allow for inter-sample variations in probe affinity or nonspecific binding to be identified and mitigated without additional tests. For low concentrations of analyte, kinetic assays could also be capable of distinguishing low-abundance specific binding from a larger background of nonspecific, or even measuring analytes below the so-called 'critical concentration' at which there is fewer than one analyte molecule bound at equilibrium—a feat impossible for endpoint assays (Squires T M et al., (2008) *Nat Biotech* 26(4):417-426).

However, single molecule kinetic measurements are technically demanding: without amplification reactions, specific binding events are more difficult to discern against a background of nonspecific interactions. Indeed, an exquisitely sensitive transduction mechanism is required to directly detect single binding events at all. A range of scientific apparatuses have been developed to investigate single molecule binding kinetics. However, none of these techniques are useful for ultra-sensitive clinical assays because the sensors are too small. To investigate nanoscale phenomena, these devices are themselves nano- or micro-scale: their active sensors are the size of single nanoparticles or nanowires (Baaske M D et al., (2014), *Nat Nano* 9(11):933-939; Besteman K et al., (2003), *Nano Lett* 3(6):727-730; Sorgenfrei S, et al. (2011), *Nat Nano* 6(2):126-132), or else they require high magnification & high numerical aperture optics with a small field of view (0.001-0.01 mm$^2$) (18-20). This is problematic because small sensors only have space for a small number of capture probes. Maximizing the number of probes is vital for ultra-sensitivity: at low concentrations, the amount of captured analyte at equilibrium is proportional to the number of probe molecules. Assay technologies therefore use large sensor areas packed with capture probes. For example, the SiMoA technology interrogates approximately 25,000 beads each 2.7 μm in diameter, corresponding to a total sensor area of 0.57 mm$^2$ (12).

There remains a need for a kinetic assay that measures the duration of individual binding events over time on a large sensor surface with a low magnification objective, while retaining the advantages of kinetic analysis such as discrimination between specific and nonspecific events based on duration (i.e., affinity).

SUMMARY

The technology described herein relates to optical biosensors and single-molecule or single-nanoparticle sensors which use a sensing surface. For example, the methods, apparatus and assays herein allow for the detection of particle surface interactions.

In one aspect the disclosure includes a method for detecting at least one particle. The method comprises providing a surface including a capture agent, providing a camera for generating an image of the surface, and providing a computer, including a memory and a processor, connected to the camera. The method further comprises flowing a solution containing particles (e.g., at least one particle) over the surface, thereby contacting the particle(s) with the capture agent, and collecting a plurality of particle-images of the surface using the camera and storing said particle-images in the memory. The method also includes analyzing the plurality of particle-images using the processor to produce a catalog of particles and time associated data for each particle in the catalog (e.g., a list of particles and associated data of the particle) and storing said catalog in the memory. The catalogue is then modified by eliminating a particle from the catalog in the memory if the time associated data of said particle does not span a time greater than a set time increment. The method also includes outputting data from the catalog as the detection of the at least one particle. Optionally, the catalogue is further manipulated wherein the method further comprises combining a first particle and a second particle in the catalog, so that said combining identifies the first and second particle as a single particle in the catalog, if said first particle is listed in a first particle-image sequence in the catalog and then not listed is a subsequent second particle-image sequence of the catalog, and said second particle is listed in a third particle-image sequence of the catalog, and wherein the time spanned by the second particle-image sequence in the catalog corresponds to less than the time increment, and wherein said combining includes assigning the time spanning the first particle-image sequence in the catalog, the second particle-image sequence in the catalog and the third particle-image sequence in the catalog to the first particle in the catalog.

Optionally the method further comprising providing a user interface and outputting said data comprises providing catalog-representative data to the user interface. For example, wherein said catalog-representative data is in the form of a text data, image data, or graphed data.

Optionally, the surface is a component in an interferometric reflectance imaging sensor (IRIS) system comprising an objective lens for illuminating a detection region of a cartridge and collecting reflected light from the detection region, wherein the detection region includes the surface. Optionally said capture agent is an antibody, a protein, a peptide an oligonucleotide, a complexing ligand, a single stranded DNA or RNA, a haptan, or a polymer. Optionally said set time increment is between one second and one hour.

Optionally said particles comprise a nanoparticle functionalized with a target, said capture agent having a high affinity for the target. For example, the target is selected from the group consisting of a small molecule, a polymer, an antibody, a haptan, an oligonucleotide, a single stranded DNA or RNA, a protein and a peptide. Optionally, the particle comprises a nanoparticle. Optionally the particle is a gold nano-particle. Optionally the particle is a virus.

In another aspect the disclosure is of an apparatus for measuring particles comprising; a surface including a capture agent, a camera for imaging the surface, a user interface for visualization of particle data, a system for flowing a solution of particles over and in contact with the surface, and a computer including a memory and a processor connected to the camera and the user interface. The camera is configured to provide a plurality of particle-images of the surface and storing said particle-images in the memory. Analyzing comprises using the processor to produce a catalog of particles and time associated data for each particle in the catalog, and storing said catalog in the memory. Analyzing further comprises eliminating any particle from the catalog in the memory if said the time associated data associated with said particle does not span a time greater than a set time increment. The computer is configured to send representative data to the user interface for visualization of catalog-representative data. Optionally, analyzing further comprises combining a first particle and a second particle in the catalog, so that said combining identifies the first and second particle as a single particle in the catalog, if said first particle is listed in a first particle-image sequence in the catalog and then not listed is a subsequent second particle-image sequence in the catalog, and said second particle is listed in a third particle-image sequence in the catalog, and wherein the time spanned by the second particle-image sequence in the catalog corresponds to less than the time increment, and wherein said combining includes assigning the time spanning the first particle-image sequence in the catalog, the second particle-image sequence in the catalog and the third particle-image sequence in the catalog to the first particle in the catalog. Optionally, the surface is a component in an interferometric reflectance imaging sensor (IRIS) system comprising an objective lens for illuminating a detection region of a cartridge and collecting reflected light from the detection region, wherein the detection region includes the surface. Optionally, the system for flowing a solution of particles includes an inlet and an outlet to the cartridge, wherein the solution flows through the cartridge from the inlet to the outlet. Optionally, the apparatus further comprising a stage for placement of the surface thereupon and configured for relative movement of the surface to the camera.

In yet another aspect the disclosure relates to a kinetic assay for the detection of single binding events, comprising flowing a solution containing particles over a capture agent functionalized surface, collecting a plurality of particle-images of the surface using a camera and storing said particles-images in a computer memory, analyzing the plurality of particle-images using a processor to produce a catalog of particles and time associated data for each particle in the catalog. The catalog is manipulated or modified by eliminating a particle from the catalog if the time associated data of said particle does not span a time greater than a set time increment. The catalog is further manipulated or modified by combining a first particle and a second particle in the catalog, so that said combining identifies the first and second particle as a single particle in the catalog, if said first particle is listed in a first particle-image sequence of the catalog and then not listed is a subsequent second particle-image sequence of the catalog, and said second particle is listed in a third particle-image sequence of the catalog, and wherein the time spanned by the second particle-image sequence in the catalog corresponds to less than the time increment, and wherein said combining includes assigning the time spanning the first particle-image sequence in the catalog, the second particle-image sequence in the catalog and the third particle-image sequence in the catalog to the first particle in the catalog. Each particle in the catalog corresponds to a binding event. Optionally, the binding event detects specific binding of the particle to the surface when the concentration of the particle is below the critical concentration. Optionally, the assay does not use a chemical amplification reaction.

The herein disclosed methods, apparatus and assay are applicable to optical biosensors and single-molecule or single-nanoparticle sensors which use a sensing surface and in some options do not require an "amplification" step before readout. These methods, apparatus and assay increase the sensitivity of single-molecule optical biosensors, and reduce assay time over other known methods. These methods, apparatus and assays also describe a single-molecule or single-nanoparticle biosensor which can measure the transient interactions of many target molecules with a sensor surface over time.

These and other capabilities of the invention, along with the invention itself, will be more fully understood after a review of the following figures, detailed description, and claims.

BRIEF DESCRIPTION OF THE FIGURES

The accompanying drawings, which are incorporated into this specification, illustrate one or more exemplary embodiments of the inventions and, together with the detailed description, serve to explain the principles and applications of these inventions. The drawings and detailed description are illustrative, and are intended to facilitate an understanding of the inventions and their application without limiting the scope of the invention. The illustrative embodiments can be modified and adapted without departing from the spirit and scope of the inventions. The patent or application file contains at least one drawing executed in color. Copies of this patent or patent application publication with color drawings will be provided by the Office upon request and payment of the necessary fee.

FIG. 9A is a plot showing naïve counting of nanorods binding to a surface.

FIG. 9B is a plot showing dynamic tracking of nanorods binding to a surface.

FIG. 9C is a histogram of nanorod dwell times showing a bi-exponential fit.

DETAILED DESCRIPTION

In general, by the technology described herein, the transient interactions of individual target-capture complexes can be monitored by measuring the dwell time of nanoparticle-labeled target molecules using as sensor surface. This approach can be realized by taking a video or movie of the sensor surface over the course of an incubation by using a micro-fluidic cartridge with a transparent window. Rather than simply counting the number of captured nanoparticles as a function of time, individual nanoparticles are tracked through the video. This way, the sensor can distinguish if a target molecule (with its nanoparticle label) leaves the sensor surface even if a new target molecule binds, since the new molecule will likely bind in a different place on the sensor. In some embodiments, this approach utilizes a Single-particle Interferometric Reflectance Imaging Sensing (SP-IRIS) substrate as the sensing surface, which is a reflective dielectric multilayer structure on silicon, for example $SiO_2$ on polished silicon.

Figure 1A:
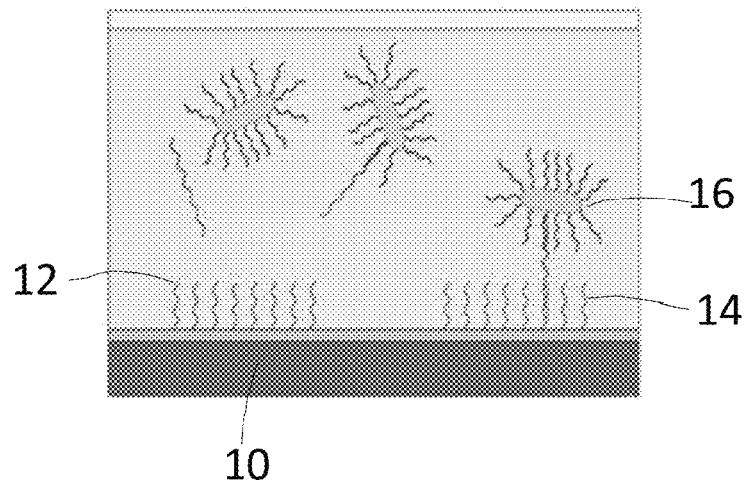
FIG. 1A is a side on pictorial view of a capture agent decorated substrate interacting with a particle.

In some embodiments a microarray of capture agents is prepared on a surface (e.g., an IRIS substrate), enabling multiplexing. FIG. 1A is a side on pictorial view of a substrate 10 that is decorated on a surface in different areas with a first capture agent 12 and a second capture agent 14. Particle 16 has a higher binding affinity to capture agent 14 and therefore is bound to the surface via the capture agent 14. Meanwhile, particle 16 has a lower binding affinity to capture agent 12 and therefore the area functionalized with capture agent 12 remains particle free, or has fewer particles bound thereto.

As used herein a capture agents or capture probes are sites on the surface or components added to a surface to which an analyte can bind. For example, the capture agent can be one part of an antigen-antibody couple (or part of antibody, e.g., Fv), ligand-receptor, enzyme-substrate, binding protein-nucleic acid or aptamer, and hybridization of nucleic acid molecules. These interactions allow for the analyte to be isolated or captured from other components in the sample.

The other part of the couple is part of the analyte, so that the capture agent can be targeted to bind to the analyte. In some embodiments the capture agent is an antibody, a protein, a peptide an oligonucleotide, a complexing ligand, a single stranded DNA or RNA, a haptan, or a polymer. In some embodiments the capture agent is a site on surface such as a cationic site or a defect that an analyte has an affinity to The analyte can be a particle such as an inorganic, metal, semiconductor, quantum dot, carbon nanotube, organic particle or molecule, biological particle or molecule or combinations of these. For example, in some embodiments the particle is a gold or other metal particle the is functionalized with a biological molecule such as a protein or a single stranded DNA. In some embodiments the particle is a virus. The particle can be of any shape such as spherical, disk-like, lozenge, prolate, rod, dendritic, faceted, or irregularly shaped. In some embodiments the particle can be a nanoparticle, for example have a dimeter between about 1 and 10,000 nm (e.g., between about 10 and 1000 nm).

In some embodiments the particle is functionalized or includes a target. As used herein a target refers to a molecule that can form a binding pair with the capture agent. For example, in some embodiments the target is selected from the group consisting of a small molecule, a polymer, an antibody, a haptan, an oligonucleotide, a single stranded DNA or RNA, a protein and a peptide. The target can even be a site on a particle such as a cationic site or a defect that a capture agent has an affinity to.

As used herein "affinity" relates to binding of the capture agent with the analyte (e.g., particle, target). The affinity can be quantified by the dissociation constant $K_d$. The dissociation constant ($K_d$) is an equilibrium constant that generally measures the propensity of a bound pair, such as a capture agent bound to an analyte, to separate (dissociate) reversibly into separate agents (e.g., the capture agent and the analyte). In these embodiments, a higher dissociation constant indicates a lower binding affinity. Alternatively, the binding affinity of a first agent for a second agent can be indicated by an association constant (K) for binding of the first agent to the second agent. The association constant (K) is the inverse of the dissociation constant ($K_d$), i.e., a higher association constant indicates a higher effective binding affinity. In some embodiments, the members of the specific binding pair have a high affinity for each other of less than or equal to $10^2$, $10^3$, $10^4$, $10^5$, $10^6$, $10^7$, $10^8$, $10^9$, $10^{10}$, or $10^{11}$ $K_D$.

Figure 1B:
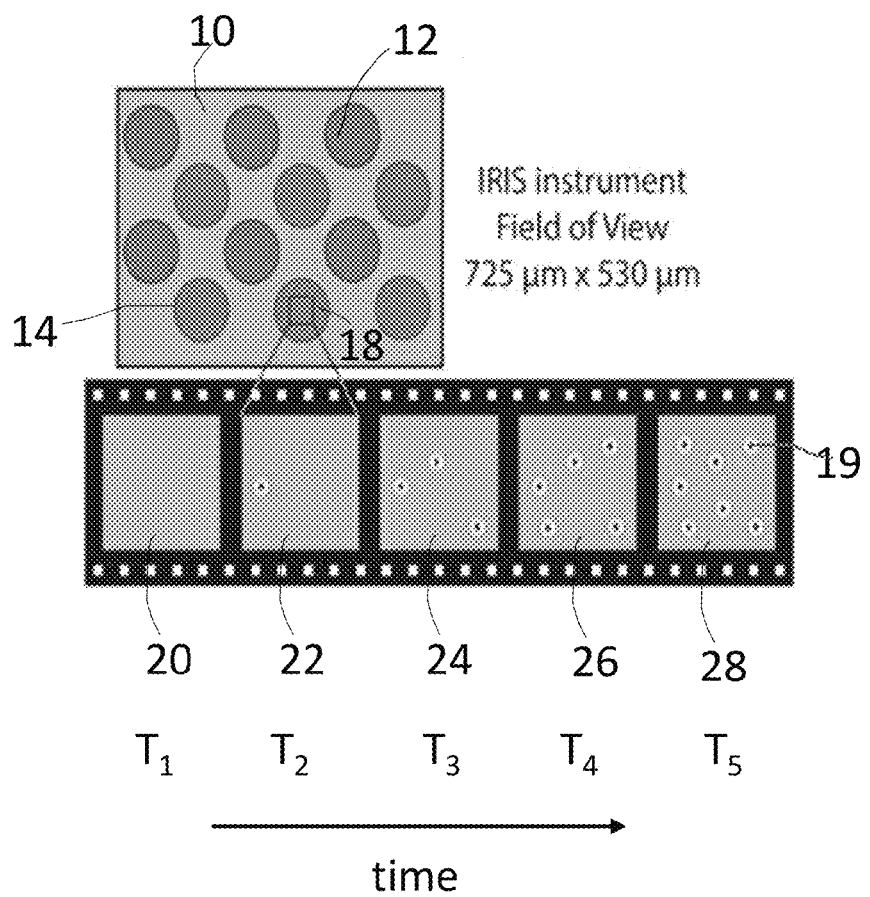
FIG. 1B shows a top view of substrate which is multiplexed with capture agents, and sequential images of an area of the substrate.

In some embodiments, the substrate is incorporated into a flow through system that allows the surface to be imaged with a widefield microscope while a sample containing the particle 16 is flowed over the chip and the particles in the solution contact the surface (e.g., a surface having capture agents). The sensing surface is imaged sequentially over time to provide a series of sequential images (e.g., a movie or video) or a plurality of particle-images. In some embodiments the imaging is with a widefield optical microscope with LED illumination. FIG. 1B shows a top view of substrate 10 which is multiplexed with at least two different capture agents, capture agent 12 and 14. An area of the substrate 18 is imaged sequentially over time, to produce a series of images. For example, the images can be time stamped or each associated with a time, such as each comprising an image for making a video. A subset of images is shown in FIG. 1B, where images 20, 22, 24, 26, 28 show the accumulation of particles 16, as blobs 19, as time increases (e.g., $T_1$, $T_2$, $T_3$, $T_4$, $T_5$). This sequence of images comprises a plurality of particle-images of the surface. Each particle-image has a time associated with it and the images span the time from $T_1$ though $T_5$. In some embodiments the field of view 18 is a field of view of about 1000 µm×1000 µm (e.g., 725 µm×530 µm).

Figure 1C:
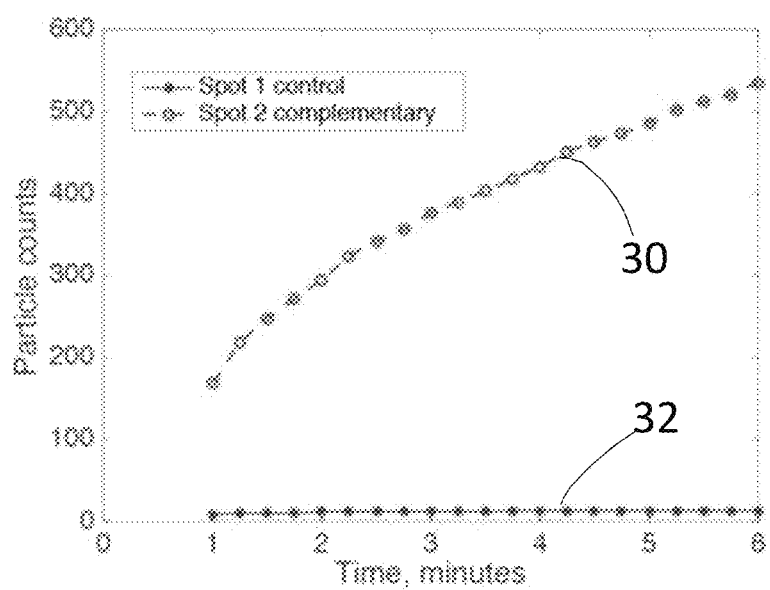
FIG. 1C is a plot showing the number of particles detected on two different areas of a substrate.

FIG. 1C is a plot showing the number of particles detected at each time. For example, each point corresponding to one particle-image with its associated time. The number of particles, such as a particle 16, on a surface area having a high affinity capture agent such as 14 is shown as curve 30. Conversely, curve 32 shows the number of particles such as 16 counted on a surface with low affinity, such as an area having capture agent 12. Both curves 30 and 32 represent "Naïve" counting, as is defined in the following.

Figure 2:
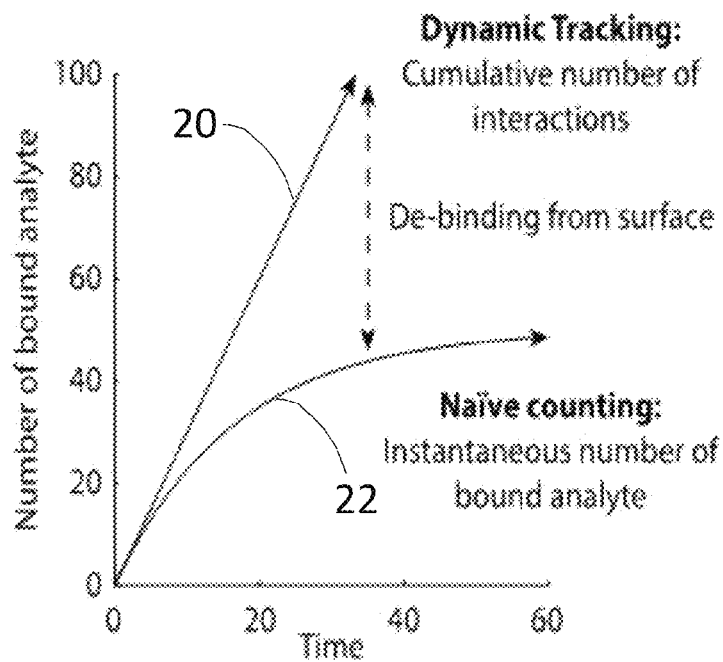
FIG. 2 is a plot showing the relationship between dynamic tracking and naïve counting 22.

FIG. 2 is a plot showing the relationship between dynamic tracking 20, which is the cumulative number of interactions between a particle and a surface, and Naïve counting 22, which is the number of instantaneous bound particles. A particle concentration can be estimated by measuring the initial slope of Naïve counting curve 22. The difference between the dynamic tracking curve 20 and Naïve counting curve 22 is the number of de-binding events. In some embodiments, where the particle concentration is very low, or the binding affinity is very low, equilibrium can be reach with very few, or even less than one, bound particle. In these embodiments, the initial slope will not be measurable. For example, in FIG. 1C an initial slope to curve 32 is difficult to identify because of the low number of bound particles due to the low binding affinity of particle 16 to low affinity capture agent 12. In some embodiments, transient particles that are not bound to the surface might be imaged as they flow over a surface in the field of view of the camera. These lead to false positives.

Figure 3A:
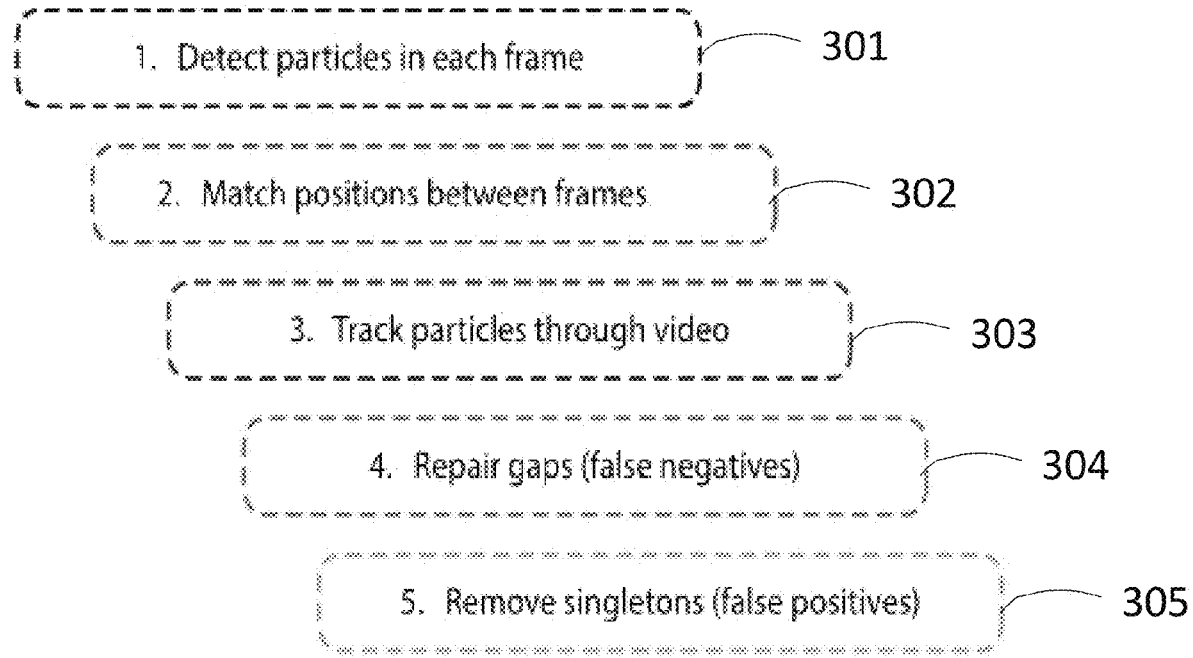
FIG. 3A shows steps for detecting the dynamic interactions of particles with a surface.
Figure 3B:
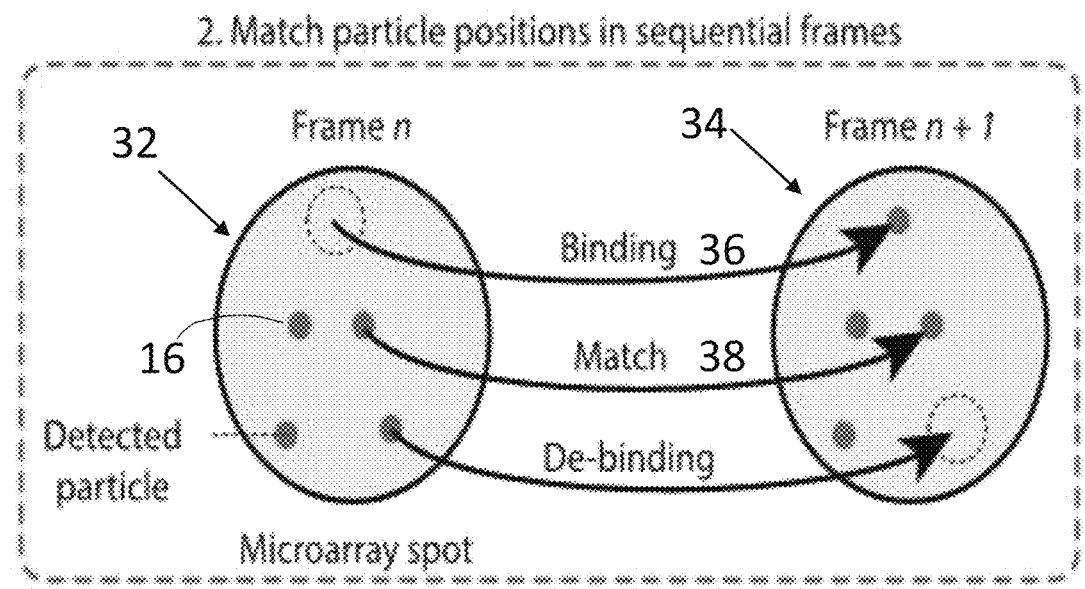
FIG. 3B shows a protocol for matching particles between frames.
Figure 3C:
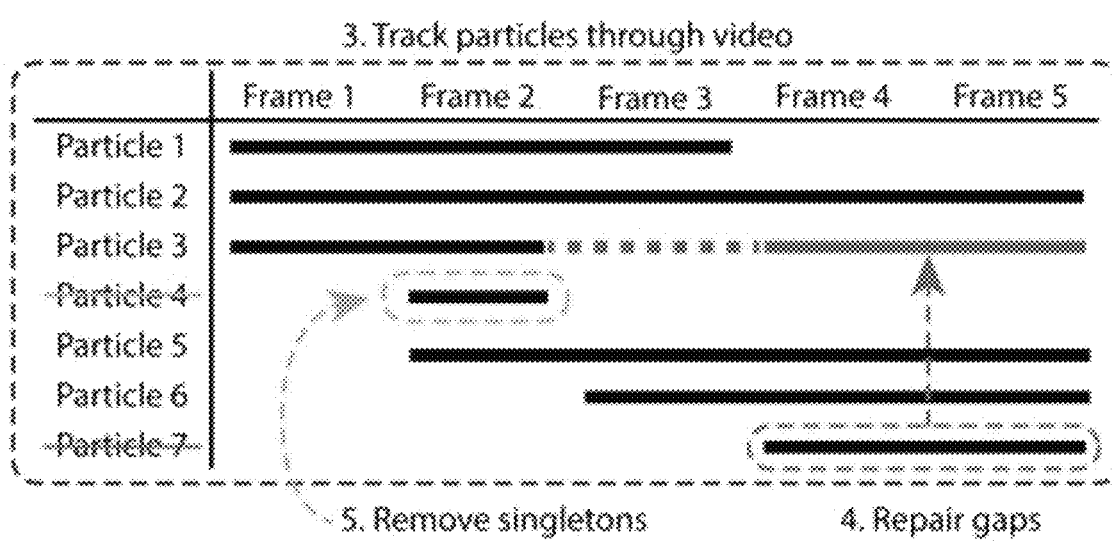
FIG. 3C is a representation of a catalog listing particles and when they are imaged or detected in the frames, and a protocol for removing singletons and repairing gaps.

A protocol or algorithm for detecting particles, even where the concentration of particle in solution is low or the binding affinity to the surface is low, is shown with reference to FIGS. 3A, 3B and 3C. This algorithm can be broken down into the five steps listed in FIG. 3A. First, 301, particles 16 are detected in each frame, for example as shown in FIG. 3B frames (Frame n) 32 and (Frame n+1) 34. Second, 302, particles 16 detected in each frame 32 are matched 38 with those in the next frame 34. This identifies every particle binding 36 and de-binding 40 event that occurred between the acquisition of frame 32 and frame 34. A binding event, 36 is identified as a particle being seen or imaged in 34, where it is not seen or imaged in 32 in the same position on the surface. A de-binding event is identified as a particle being imaged in 32 and then not seen or imaged in 34 in the same position on the surface. In a third step, 303, these data are collected into a single particle list or catalog, shown as FIG. 3C, which lists the binding and de-binding times of every particle that interacted with the surface during the experiment. Thus this list is a list of particles and time associated data for each particle.

Steps 304 and 305 are steps for culling the particle list or catalog of false positive and false negative particles. An embodiment of these steps is illustrated with reference to FIG. 3C. In step 304, the particle list is repaired by identifying gaps where particular nanoparticles were not detected for a period or span of time, such as in the time span or gap associated with two sequential frames (i.e., false negative). The period of time can be a set time increment such as set by an operator. The operator can set this time increment based on the expected interaction between the particle and surface and can be, for example between about one second and one hour. For example, particle 3 is imaged in frame 1 and frame 2 (e.g., a first particle listed in a first particle-image sequence in the catalog), then not seen in frame 3 through frame 5 (e.g., a second particle-image sequence in the catalog). In the same position on the surface as particle 3, particle 7 is seen only in frame 4 and frame 5 (e.g., a second particle listed in a third particle-image sequence in the catalog). Since particle 3 and 7 are in the same position but separated in time, the repair algorithm assigns particle 3 and particle 7 to one particle, particle 3 (e.g., the first particle), and deletes particle 7 from the list. particle 3 is also assigned the entire time spanning frames 1 through frame 5 (the time spanning the first particle-image sequence in the catalog, the second particle-image sequence in the catalog, and the third particle-image sequence in the catalog), thereby repairing the "gap" in frame 3. The particle list in step 305 is also purged of nanoparticles only detected less than an expected time span, (e.g., a set time increment such as time for binding) such as in just the time associated with one frame (i.e., false positives). For example, particle 4 is seen only in frame 2 and is deleted as a non-binding event. In some embodiments each frame is not a single image but represents a collection of images that span a time.

In some embodiments the set time increment can be the time designated as a time corresponding to less than a binding event, where at least two frames are identified as spanning a time where a particle is considered to be bound to the surface. In some embodiments the time increment is a constant value. In some embodiments a collection of two or more frames forms a video or movie of the particles as they interact with the surface. In some embodiments each frame is represented by a list of data, e.g., text data, such as brightness, size, shape, time and position rather than a visual image.

In some embodiments, the output of this method as describe with reference to FIG. 3A-3C is a refined particle list data structure, or catalog, which has useful properties. For example, the cumulative rate of particle binding can be easily found, which greatly improves the sensitivity of the system to weakly-binding analytes for the reasons described above. Second, the dwell time of each particle on the sensor can be measured.

In some embodiments, a protocol or algorithm for detecting particles can be accomplished using a computer and a camera and the following three steps. In a first step, a camera collects several images in a field of view and saves the images. A computer then processes the images using imaging software. The particles are then tracked using calculation software. The imaging software identifies the position of each particle and creates a directory of text file with particle position coordinates. The calculation software goes through the text file of coordinates and creates the particle catalog, eliminating false positives and false negatives based on the particle positions and durations on the surface as indicated in the text files. In some embodiments the calculation software uses a clustering function to account for any unintended movement of the surface and particle relative to the camera, for example, from unwanted or unintended vibrations. In some embodiments the clustering function uses a k-means algorithm.

In some embodiments the imaging software can be ImageJ which is available at www.imagej.nih.gov/ij/index.html (accessed Apr. 29, 2019). In some embodiments the calculation software is MATLAB® available from Math-Works® (www.mathworks.com/products/matlab.html accessed Apr. 29, 2019).

In some embodiments at each "time point" a stack of images is taken, where each image in the stack has a different focal plane. This can be done by moving a stage relative to the camera. The first step of analysis is to find the particle since in some embodiments the particles are not always in focus. This stack can be combined to render the text file of particle coordinate positions as described above, and or can be combined to render an image such as shown in FIG. 3B as 32 and 34. In some embodiments between 1 and 50 images are taken, where each image takes between 0.1 and 30 seconds. For example, between 6 and 20 images are taken with between 1 and 10 seconds between each images. This stack of images is clustered as a time point and between each time point there can, in some embodiments, be a delay of several seconds, several minutes or even several hours. For example, in some embodiments the time points are between 1 second and 1 hour.

As used herein a computer includes a processor, memory and input/output peripherals. The input/output peripherals can include a user interface such as a mouse, keyboard, touch pad as well as a graphical user interface such as a monitor. The memory can include read-write as well as DRAM memory. The processor can also include wireless connections (e.g., WiFi, Bluetooth and Zigbee), for example to connect to the peripherals or to connect to local or non-local networks. The computer also includes software such as a Windows operating system and data manipulation and gathering and visulization software. In some embodiments the computer is connected to an imaging system, such as an SP-IRIS imaging system, and via the input and outputs operates the imaging system. In some embodiments the computer also includes microprocessors, for example, to control flow to a flow cell, the movement of a stage, illumination of the detection surface or the temperature of the flow cell. In some embodiments more than one computer is used, such as a first computer for controlling hardware and data collection and a second computer for manipulation of collected data.

Figure 4:
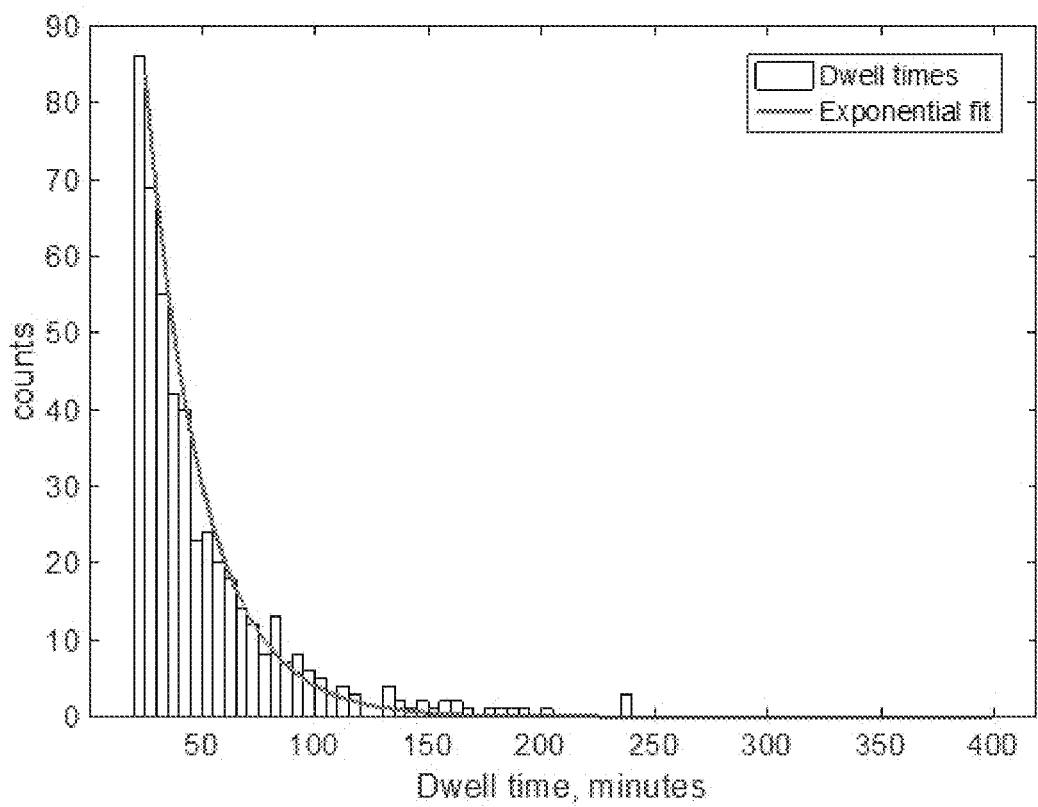
FIG. 4 shows a histogram of particle dwell times fit to an exponential function.

In some embodiments a computer is used to modify or process the catalog data or particle list and provides catalog-representative data. For example, the catalog representative data can include text data, image data, or graphed data. For example, FIG. 4 shows a histogram of particle dwell times (catalog-representative data) found by the methods as described herein. The histogram can be fit to an exponential function, the decay constant of which is the dissociation time constant of the particle to the surface. In some embodiments therefore, the decay time constant can be found and outputted by the computer interface as catalog-representative data.

In some embodiments, the catalog data or catalog representative data is kinetic data. As used herein "kinetic data" or "kinetic assay" relates to particle binding events such as the rates of binding and de-binding of particles to the surface. In some embodiments where a low concentration of analyte (e.g., particles) are used, the kinetic assays as described herein are capable of distinguishing low-abundance specific binding from a larger background of nonspecific, or even measuring analytes below the "critical concentration" which is the concentration at which there is fewer than one analyte molecule bound at equilibrium.

As used herein "specific binding" is the binding of the capture agent to the analyte (e.g., particle or target). "Non-specific binding" is binding that occurs due to other interactions that are unintended and can be a component of background noise. For example, Non-specific binding refers to the binding of an analyte to something other than its designated capture agent.

Figure 5:
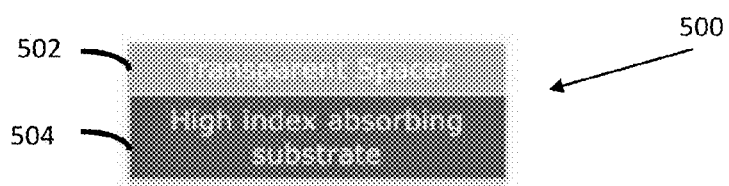
FIG. 5 shows a configuration of the sensor chip.

In some embodiments the methods utilize Interferometric Reflectance Imaging Sensor (IRIS) substrate as the sensing surface. IRIS is a biosensor modality that requires high quality optical images acquired as analytes bind to the sensor surface. These images are acquired through the top window. The sensor chip itself has specific requirements including (i) flat and smooth surface that can be chemically functionalized and (ii) a multi-layer (at least two dielectric layers) structure to facilitate interference signature and (iii) desirably an absorbing substrate to eliminate any stray light. A basic configuration of the sensor chip is shown in FIG. 5. The substrate 500 includes a top transparent spacer 502 which provides the spectral signature for the IRIS. The top layer has a relatively low refractive index to achieve high sensitivity sensing of binding particles, such as gold nanorod, biological particles and molecules on the surface. Due to the low refractive index of common biological molecules and particles, for example refractive index for viruses and proteins is around 1.5, for exosomes is around 1.4, it is desirable to have the top layer of the IRIS sensor to have a comparable refractive index. The bottom part of the substrate 504 can have a higher refractive index providing the reflection of the reference optical field and it is desirable to have an absorbing material to eliminate stray light. One nearly ideal configuration for sensors operating with visible light is silicon oxide or silicon nitride coated Si substrates. Typical silicon oxide and silicon nitride, and their combinations provide refractive indices in the range of 1.45 to 2.3 in the visible spectrum of light.

Figure 6:
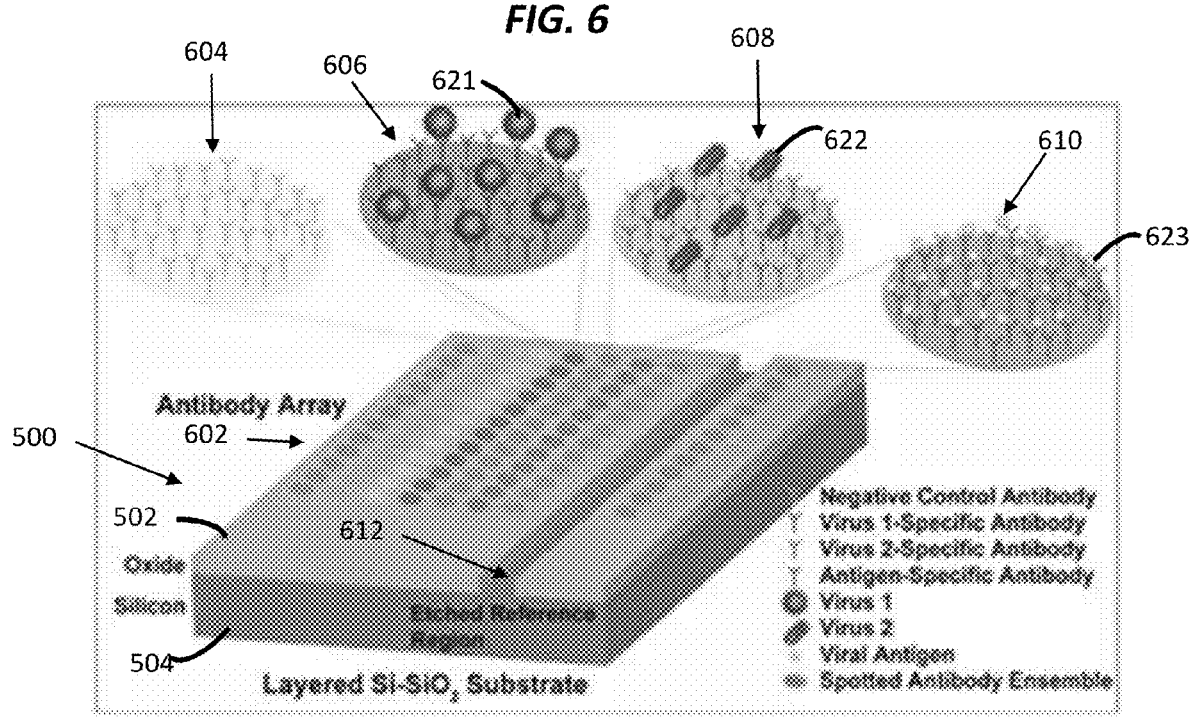
FIG. 6 illustrates an embodiment of a configuration for a sensor chip having a surface functionalized with capture agents.

As illustrated in FIG. 6, in some embodiments, a top surface of silicon oxide 502 (or silicon nitride) can be functionalized readily and capture agents for multiplexed detection of particles can be arrayed on the surface. Some features shown include an antibody array 502, over the layered silicon/silicon oxide substrate 500 on the transparent layer 502 where the array can include negative control antibodies 604, a first virus specific antibody 606 shown with a first virus, a second virus specific antibody 608 shown with a second virus, and an antigen specific antibody 610 shown with a viral antigen. An etched reference region 612 is also shown. In this illustration the particles are biological e.g., a first virus 621, a second virus 622, and a viral antigen 623.

Figure 7:
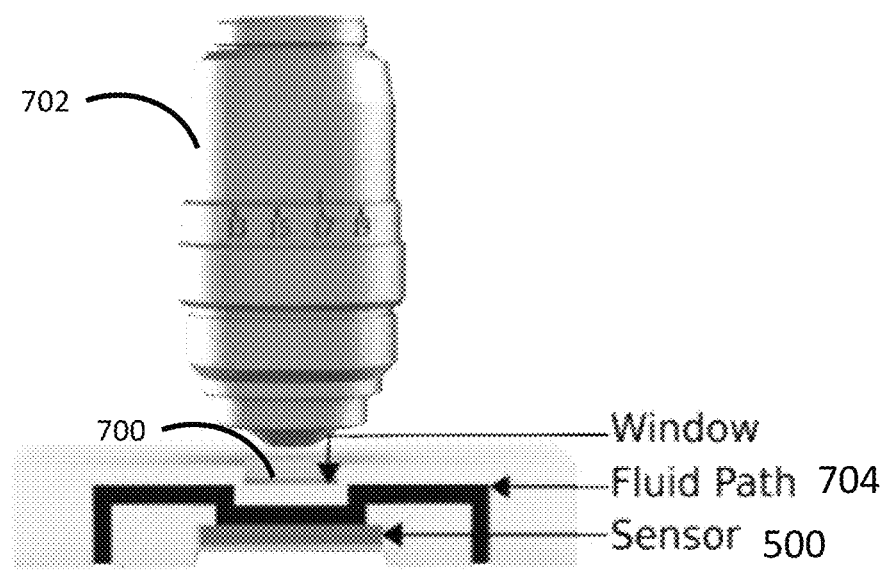
FIG. 7 shows a schematic drawing of a microfluidic cartridge.

FIG. 7 shows a schematic drawing of a microfluidic cartridge illustrating how the sensor chip is incorporated in the incubation chamber and sensor surface is imaged through a transparent window. The substrate 500 and window 700 are shown as well as an optical imaging apparatus component 702 and a fluid flow path 704. In some embodiments the optical imaging component 702 includes a camera. In some embodiments, the substrate and cartridge are mounted on a stage so that the substrate can be moved relative to a lens of a camera of imaging component 702. The microfluidic cartridge for SP-IRIS is disclosed in commonly owned International Application (designating the U.S.) nos. PCT/US2010/033397, PCT/US2014/062605 and PCT/US2015/019136, which are hereby incorporated by reference, in their entirety.

Figure 8A:
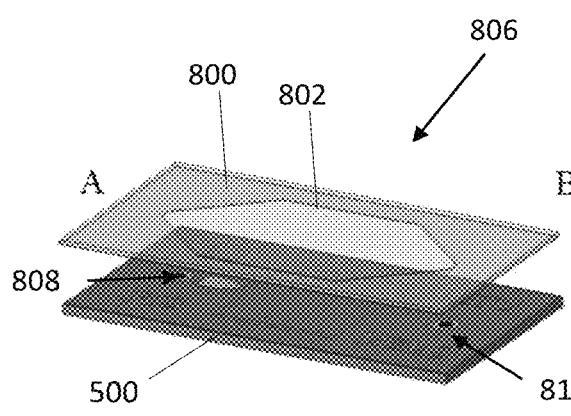
FIG. 8A shows a blown up view of an embodiment of a cartridge.
Figure 8B:
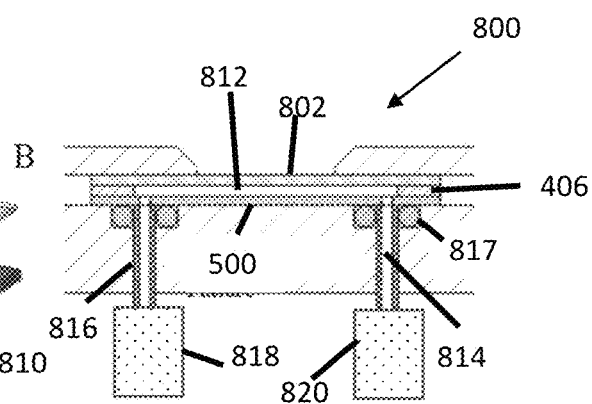
FIG. 8B shows a front cross cut view of the cartridge shown in FIG. 8A in a clamping apparatus.
Figure 8C:
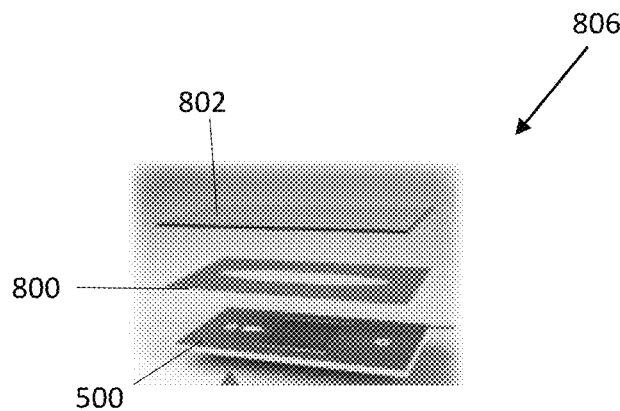
FIG. 8C shows another blown up view of the cartridge shown in FIG. 8A.

Optionally, in some embodiments using a surface for detection/binding of particles, the surface is a region of a cartridge. FIG. 8A shows a blown up view of an embodiment of a cartridge 806, while FIG. 8B shows a front cross cut view of the cartridge in a clamping apparatus 800. FIG. 8C shows another blown up view of the cartridge. The cartridge includes a substrate 500 which can be a silicon substrate. The cartridge also includes a cover window 802 including a transparent portion and a spacer 800. In some embodiments the window is a cover glass or any other flat window material. The substrate also includes ports 808 and 810 which are holes etched, cut, or drilled through Si substrate to facilitate liquid flow therethrough. The spacer of the cover window is configured to contact a substrate face so that the transparent portion and spacer define a channel 812 extending between the ports 808 and 810. The clamping apparatus can include fluid conduit 814 which can engage with the port 810, and fluid conduit 816 which can engage with port 808. The clamping apparatus can also include sealing elements 817 (e.g., O-rings). In some embodiments, the channels can be connected to a fluid source and sink, for example, a first reservoir 818 connected to a pump for pumping fluid into fluid conduit 816, through port 808, through channel 812, through port 810, through channel 814 and to a second reservoir 820. In embodiments using cartridges for the detection of particles on surfaces, the cartridge provides a method of flowing particles over the surface to be detected, for example using SP-IRIS, so that dynamic measurements of particle interactions as described herein can be made.

In some embodiments the the dimensions and configurations can be selected for IRIS or SP-IRIS as taught in International Application (designating the U.S.) nos. PCT/US2006/015566, PCT/US2010/033397, PCT/US2014/062605, PCT/US2015/019136, and PCT/US2018/064927 which are hereby incorporated by reference, in their entirety.

As used herein "chemical amplification" refers to methods for detecting an interaction or molecule where the direct detection might not be detectable or visible without amplification. For example, Polymerase Chain Reaction (PCR) or the conjugation of a reporter molecule such as HRP to avidin and streptavidin in enzyme-linked immunosorbent assay (ELISA). In some embodiments, the methods and technologies herein do not require or use a chemical amplification for detection of binding events.

In other embodiments of the technologies for detection of binding between a capture agent and an analyte the technique could use a different sensor surface material (such as a transparent substrate). In some embodiments a different readout method for imaging single nanoparticles such as imaging surface plasmon resonance. In some embodiments, highly-efficient fluorescent labels or quantum dots could be used. In some embodiments any technique which could enable the detection of single molecules immobilized on a substrate in a video lasting minutes or hours could be used.

As used herein the term "comprising" or "comprises" is used in reference to compositions, methods, and respective component(s) thereof, that are essential to the claimed invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the claimed invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Other embodiments are within the scope and spirit of the invention. Further, while the description above refers to the invention, the description may include more than one invention.

The embodiments will be more readily understood by reference to the following examples, which are included merely for purposes of illustration of certain aspects and embodiments of the present invention, and should not be construed as limiting. As such, it will be readily apparent that any of the disclosed specific constructs and experimental plan can be substituted within the scope of the present disclosure.

EXAMPLES

Summary

The clinical need for ultra-sensitive molecular analysis has motivated the development of several endpoint assay technologies capable of single molecule readout. These endpoint assays are now primarily limited by the affinity and specificity of the molecular recognition agents for the analyte of interest. In contrast, a kinetic assay with single molecule readout as describe herein can distinguish between low abundance, high affinity (specific analyte) and high abundance, low affinity (nonspecific background) binding by measuring the duration of individual binding events at equilibrium.

Herein is described such a kinetic assay, in which individual binding events are detected and monitored during sample incubation. This method uses plasmonic gold nanorods and interferometric reflectance imaging to detect thousands of individual binding events across a multiplex solid phase sensor with a large area. In this study, a 20×, 0.45 NA objective and a 1.1" format camera which yielded a sensor area of 0.38 mm$^2$ was used. A dynamic tracking procedure was used to measure the duration of each event. From this, the total rates of binding and de-binding as well as the distribution of binding event durations are determined. A limit of detection of 19 femtomolar for a synthetic DNA analyte in a 12-plex assay format was obtained.

Results

Detection of Individual Binding Events Across a Large Field of View.

A 'digital microarray' assay technology can rapidly enumerate individual captured molecules across hundreds of microarray spots (Sevenler D et al. (2018), *ACS Nano* 12(6):5880-5887). This technology uses probe-conjugated gold nanorods as molecular labels, and an interferometric reflectance imaging sensor (IRIS) to rapidly detect individual nanorods with a low-magnification (10×-20×) objective. The large field of view enables a similar throughput to commercial fluorescence readers while enhancing the limit of detection and dynamic range by a factor of approximately 10,000. The assay reaction is based on the bio-barcode assay developed by others (Hill H D et al., (2006), *Nat Protoc* 1(1):324-336) and is compatible with a range of different analytes.

The IRIS digital microarray platform was used for dynamic measurements by designing a perfusion chamber that consists of an IRIS chip, a patterned silicone gasket, and an antireflection-coated coverglass window. Two holes for the chamber inlet and outlet are drilled in the IRIS chips by wafer-scale laser micromachining. The assembly is held by a custom clamp fixture that makes fluidic connections to the inlet and outlet on the bottom of the chip.

To demonstrate dynamic detection of single molecules, a synthetic ssDNA oligonucleotide was used as a proof-of-concept analyte. The analyte was pre-incubated with complementary DNA conjugated gold nanorods nominally 25 nm×70 nm for ninety minutes. The concentration of nanorod labels was kept constant for all experiments at 14 pM while the concentration of the analyte varied from 10 pM to 10 fM. After pre-incubation, the mixture was perfused over IRIS chips with DNA microarrays of complementary and noncomplementary probes, and nanorod-labeled oligos hybridized to the complementary spots.

Images were acquired every 30 seconds with the IRIS instrument during perfusion. Nanorods on the IRIS chip were visible as faint diffraction-limited blobs in the images, which were detected in each frame independently using custom software. The binding rates were then measured using a custom Dynamic Tracking algorithm described in the following section.

IRIS detects individual nanorods based on light scattering. Since water has a higher refractive index than air, the polarizability and scattering cross section of the nanorods were reduced compared with dry chips. Additionally, the image suffered from spherical aberrations caused by the air-coverglass interface. Although nanorods were detectable with a 10×, 0.3 NA objective, visibility was much improved with a 20×, 0.45 NA coverglass corrected objective. The resulting field of view of 0.38 mm$^2$ (725 µm by 530 µm) could comfortably accommodate 12 microarray spots each approximately 80 µm in diameter.

Dynamic Tracking of Binding Events Over Time.

Under sufficiently high flow rates, the initial rate of binding of analyte is proportional to the bulk analyte concentration. An estimate of the analyte concentration can be obtained by plotting the number of bound nanorods over time, and measuring the initial slope (Naïve counting). However, this approach has several shortcomings. The first is the fundamental issue related to finite probe affinity mentioned earlier. Ultra-low analyte concentrations will reach equilibrium with very few (or even less than one) bound molecules. In those cases, the initial slope will not be measurable even with perfect error-free readout. The second issue is that some unbound nanorods are visible in each frame as they transiently diffuse through the detection volume. These transient particles result in false positives that increase the overall noise floor of the sensor.

To address these issues, a post-processing algorithm that uses the spatial positions of particles to track them individually over the course of the experiment was developed. First, particles are detected in each video frame independently of other frames, and their positions in the image are recorded. Second, these positions are compared with those of particles in the next frame of the video. Particles in the same position in both frames are 'matched', indicating that they are in fact the same particle. Particle matching includes a clustering algorithm that is robust to small translations between frames. For a video with N timepoints, this results in N−1 lists of matches. Third, these lists are compiled into a single master catalog which tracks the contiguous series of frames in which each particle was observed. This is essentially a table which lists when each particle bound, where it bound, and when (if ever) it de-bound from the surface. Finally, this catalog is filtered to reduce false positives and false negatives. False negatives occur when a particle is mistakenly not detected in a single frame but was detected in the same position in previous and subsequent frames. This erroneously results in two entries in the catalog. These gaps are repaired by identifying whether the binding of each particle corresponds to the exact same place as the de-binding of another particle two frames prior, and then merging the two catalog entries. False positives are caused by particles visible in just one frame, and are simply removed.

This catalog can then be used to plot the rate of new binding events. For low analyte concentrations, most of the available binding sites will remain empty at equilibrium and the rate of new binding events will be constant and proportional to the bulk concentration. At an analyte concentration of 316 fM for example, the sensor reached equilibrium with about eighty bound nanorods after one hour (FIG. 9A). As predicted, the binding rate of nanorod-labeled analyte was constant over time, even after equilibrium was reached ("Total binding", FIG. 9B). Note that the total number of binding and de-binding events are both cumulative measurements and are therefore monotonically increasing over time.

The measured rates of binding were compared with the predicted rates of transport of analyte-bound nanorods to the spots. The measured rate of binding was well below the theoretical upper limit predicted by mass transport. The maximum expected binding rate was also experimentally characterized with a series of control experiments in which the nanorods irreversibly bound directly to the microarray spots. In these control experiments the rate of de-binding was negligible, so the instantaneous and cumulative binding rates were nearly identical and linearly proportional to nanorod concentration.

Measurements of Nanorod Dwell Times.

The duration or 'dwell time' of each binding event can be measured using dynamic tracking. Note that the dwell time can only be measured for particles which did de-bind before the end of the experiment. Taken together, these dwell times allow the off rate $k_{off}$ of the nanorods to be determined (FIG. 9C). It was found that the experimental results were best explained by a bi-exponential fit of the form $N(t)=A_1 e^{-k_1 t}+A_2 e^{-k_2 t}$. A histogram of dwell times across all complementary spots was generated for each experiment and fitted independently. Ignoring experiments that were too brief or contained too few binding events to have meaningful statistics, the fitting parameters were consistent across experiments regardless of analyte concentration. The average values were $k_1=0.53$ min$^{-1}$ and $k_2=0.082$ min$^{-1}$ and $A_1/A_2 \approx 25$, corresponding with primary and secondary dissociation time constants $\tau_1=1.9$ min and $\tau_2=12$ min. At first, it was hypothesized this heterogeneity was consistent of nanorods tethered by either one versus two or more analyte molecules. However, this hypothesis was not supported by two observations: the relative weights between the two terms $A_1/A_2$ was similar across a large range of concentrations, and the ratio did not tend to decrease with lower analyte concentrations. Since the total nanorod concentration was kept constant at 14 pM, the relative number of nanorods with two bound analytes versus one bound analyte would have decreased with decreasing analyte concentration.

As an alternative, it was hypothesized that the bi-exponential distribution in dwell times was caused by the asymmetry of the nanorods themselves as they bind to the surface. Note that the binding energy is likely greater if the rod is tethered to the surface by one end, rather than by the middle. First, there is electrostatic repulsion between the DNA-functionalized nanorods and the DNA-coated chip surface. A side-tethered nanorod is constrained in a manner that brings the centroid closer to the chip and brings a larger surface area adjacent to the chip. Second, the end-tethered nanorod has a larger number of conformational degrees of freedom (three rotational DOF) than a side-tethered one (one rotational DOF), resulting in a lower entropic penalty to binding. Since the rods are functionalized uniformly across their surfaces, nanorods are more likely to capture analyte to their sides rather than ends during pre-incubation, and therefore be side-tethered. This is supported by the observation that the faster dissociation rate was more prevalent across all concentrations.

Detection Below the Critical Concentration.

Figure 10B:
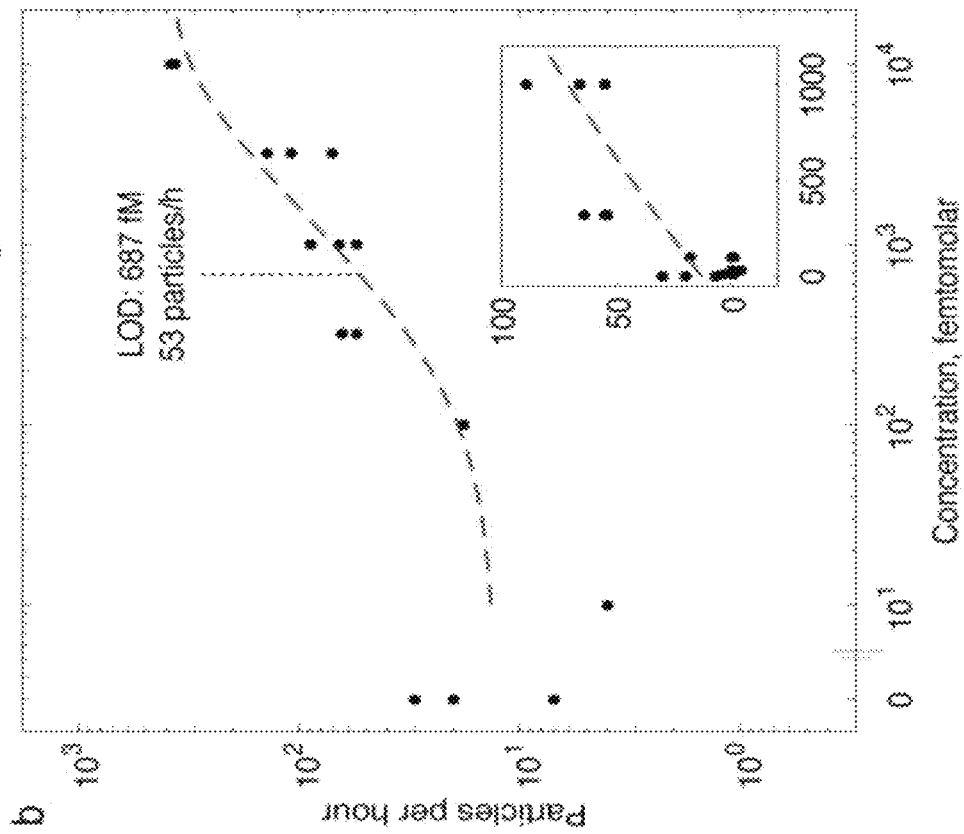
FIG. 10B is a plot showing naïve counting for nanorods below the critical concentration.
Figure 10A:
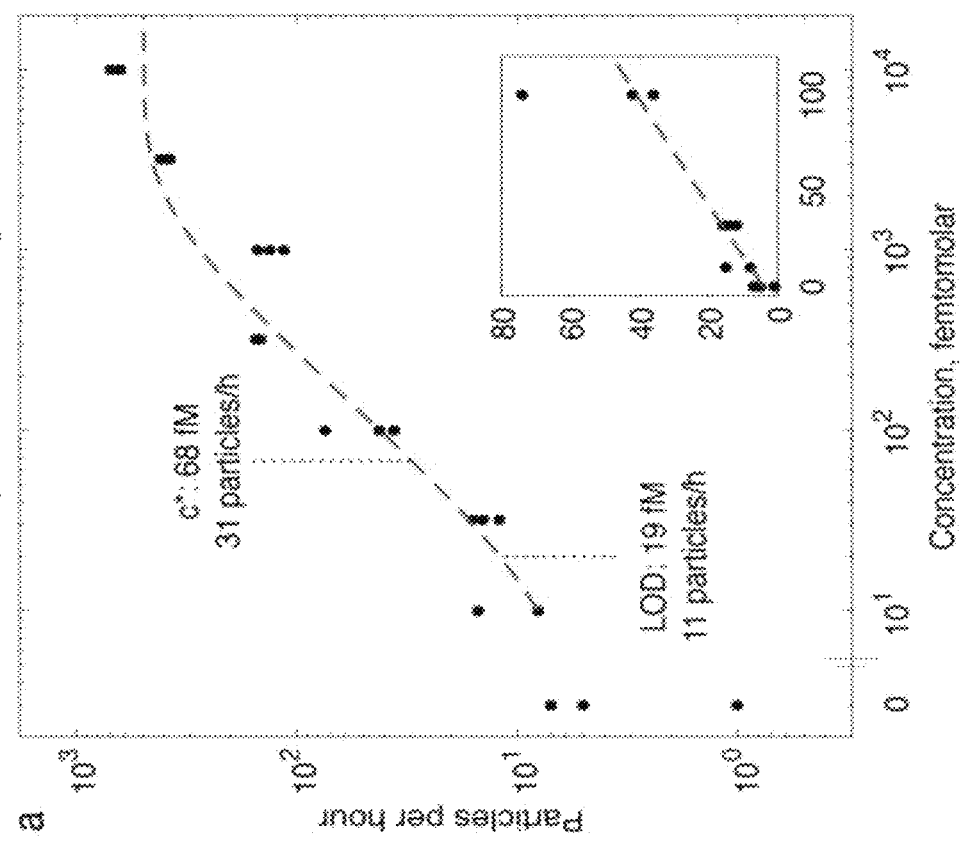
FIG. 10A is a plot showing dynamic tracking for nanorods below the critical concentration.

A standard curve was measured by performing identical experiments with a range of analyte concentrations between 10 fM and 10 pM. Nanorod binding to three complementary spots were analyzed using both dynamic tracking and naïve counting (FIGS. 10A and 10B). A modified Langmuir adsorption model was fit to the data. The Limit of Detection was calculated as three standard deviations above the mean signal from the blank sample. As expected, the limit of detection for dynamic tracking (LOD=19 fM) surpassed that of naïve counting by over a factor of 30 (LOD=687 fM). The modified Langmuir model is described in detail below. In brief, the canonical model was modified to predict a saturation in binding rate as the analyte concentration approaches the concentration of nanorods.

Notably, dynamic tracking had a limit of detection 3.6 times lower than the critical concentration of this assay (c*, FIG. 10A). Equivalently: dynamic tracking was able to detect the presence of the analyte even when the average duration of binding events was shorter than the time between them. At the critical concentration, equilibrium is reached with one bound analyte molecule on average. This dissociation rate is simply the weighted average of the two dissociation constants found earlier: $k_{off}=(A_1 k_1+A_2 k_2)/A_1 A_2=0.52$ min$^{-1}$=31 particles per hour. The critical concentration was found by taking intercept of the dynamic tracking regression line with this binding rate: c*=55 fM. Therefore, sensitivity was limited by nonspecific binding rather than insufficient probe number even in this 12-plex assay format.

Estimation of the Rate of Mass Transport:

The rate of transport of analyte-captured gold nanorods to the sensor surface was estimated as previously described (Squires T M et al., (2008), *Nat Biotech* 26(4):417-426 which is herein incorporated by refernce).

The flow cell cross section is a rectangular channel, width $W_c=4$ mm and height $H=150$ μm. Each microarray spot was approximately 75 μm in diameter, which we approximate as an equal-area square $L=W_s=66.5$ μm. The sensor to channel height ratio was therefore $$\lambda = \frac{H}{L} = 2.25.$$

The volumetric flow rate Q was 10 μl/min. The diffusion coefficient of the nanorods was estimated based on kinetic theory (below) to be 6.6 μm$^2$/s.

Assuming that all analyte hybridize to nanorods before flow begins, the rate of target-hybridized nanorod interactions with each microarray spot can be predicted based on mass transport. The channel Peclet number $$Pe_H = \frac{Q}{W_c D} \approx 6300$$

is large, suggesting that convection is much faster than diffusion and the depletion layer is small compared to the chamber height. The shear Peclet number $Pe_S = 6\lambda^2 Pe_H = 1.9 \times 10^5$ is also very large, indicating the depletion layer is very thin compared to the sensor itself, i.e., the sensor is not really depleting the sample at all. Only target-hybridized nanorods that happen to be very close to the surface (within about 1 µm) have a chance of being captured.

The flux of target-hybridized nanorods to the surface is therefore linearly proportional to the bulk concentration $c_0$ as $$J_D \approx 0.81\, Pe_s^{\frac{1}{3}} W_s D c_0.$$

A target concentration of 100 fM would correspond with a flux of about 1.8 particles per second per spot, or roughly 6,500 particles per hour per spot. The observed binding rate in the assay was about 0.5% of this theoretical upper limit, and roughly 2% of this limit for the 'direct binding' control.

Modified Langmuir Adsorption Model:

Dynamic Tracking measures the concentration of the analyte via the concentration of nanorod-analyte complexes. The number of complexes is not necessarily linear with analyte concentration: as the analyte concentration approaches that of the nanorods, the number of nanorods with at least one bound analyte will taper off.

This is can be described with a modified Langmuir adsorption model. In the canonical model the proportion of occupied binding sites at equilibrium is determined by the concentration of the analyte and the dissociation constant $K_D$. At concentrations below $K_D$ the system is starved of analyte and the number of complexes is linear with analyte concentration. Above $K_D$ the system is instead starved of empty binding sites, resulting in saturation.

In this assay each nanorod contains dozens to hundreds of binding sites, so the measurement (the concentration of nanorods with at least one analyte) can saturate far below $K_D$. When the analyte concentration is similar to or lower than the nanorod concentration, the concentration of nanorods with at least one analyte is weighted by a Poisson distribution:

$$G_{bound}(c) = G_0\left(1 - e^{-\frac{c}{G_0}}\right)$$

Here, c is the analyte concentration and $G_0$ is the total nanorod concentration. When $$c \ll G_0,\ 1 - e^{-\frac{c}{G_0}} \approx \frac{c}{G_0}$$

and $G_{bound}(c) \approx c$. On the other hand, $G_{bound}(c) \approx G_0$ when $c \gg G_0$. This model shares the same limit behavior as the canonical Langmuir model.

Since other experimental evidence suggested the nanorod concentration was substantially lower than 14 pM we left $G_0$ as a fitting parameter, along with linear offset and scaling parameters m and b:

$$R(c) = m G_{bound}(c) + b$$

Note that this model does not account for the fact that nanorods with multiple analyte will likely have increased $k_{on}$ and decreased $k_{off}$.

Diffusion Coefficient of the Nanorods:

The total translational diffusion coefficient of the DNA-coated nanorods was approximated based on Stokes-Einstein equation from kinetic theory. For a spherical particle of radius r, the diffusion coefficient is given by $$D_{sphere} = \frac{k_B T}{6\pi \eta r}$$

where r is the particle radius, η the solvent dynamic viscosity and $k_B T$ the particle's average thermal energy. For a spheroid, the diffusion coefficient must be adjusted by a 'friction factor' first described by Perrin (2) that depends on the particle aspect ratio:

$$D_P = \frac{D_{sphere}}{f_P}$$

Here $D_{sphere}$ is the diffusion coefficient of a sphere of equivalent volume. The friction factor for a prolate spheroid is calculated from the particle aspect ratio p=a/b, where a and b are the spheroid major and minor axes respectively (a>b), by (3)

$$f_P = \frac{\sqrt{p^2 - 1}}{p^{\frac{1}{3}} \ln\left(p + \sqrt{p^2 - 1}\right)}$$

Although gold nanorods tend to be rod-shaped rather than prolate, the error is small when p<10 (3). The bare gold nanorods in these experiments were nominally 25 nm by 71 nm, and functionalized with a dense coat of ssDNA 30 nucleotides long. Immobilized DNA in the coat are thought to extend outwards due to electrostatic repulsion from each other (4, 5). We somewhat arbitrarily estimated the thickness of this coat as 10 nm based on the known relation for rigid double-stranded dsDNA of 0.34 nm per base pair. For the purposes of estimating their diffusion coefficients therefore, rods were estimated as 45 nm by 90 nm prolate spheroids with p=2, $f_p$=1.05. A sphere of equivalent volume would have a radius of r=31 nm, giving $D_{sphere}$=6.9 µm²/s. and $D_p$=6.6 µm²/s.

DISCUSSION

Based on the canonical Langmuir adsorption model, equilibrium between with the liquid phase analyte and the sensor surface is reached within a time approximately equal to that of the dissociation time constant of the analyte from the surface. Probe-analyte complexes with low affinity have short dissociation time constants, and therefore reach equilibrium relatively quickly. This limits the ultimate sensitivity of some microarrays, since a dilute target species may reach equilibrium with very few (or even none) captured on the sensor on average. The recently described development of a ultra-sensitive biosensing technique called Single-particle Interferometric Reflectance Imaging Sensing (SP-IRIS), can detect the binding kinetics of biological nanoparticles such as viruses (Scherr et al, ACS Nano 2016). This technology enables transport rate limited detection of even weakly binding targets which would otherwise be reaction rate limited. The approach is based on the fact that even during equilibrium, the sensor continues to capture new target molecules while previously captured targets de-bind. If the binding of new targets can be robustly discriminated from the de-binding of previously captured molecules, the cumulative number of probe-target interactions can be monitored, instead of just the instantaneous number. Even after equilibrium has been reached, the cumulative number of interactions will increase at constant rate that is proportional to the target molecule concentration.

A range of endpoint assay technologies have been developed that have single molecule readout. For these assays, the limiting factor is the affinity and specificity of the molecular recognition agents rather than readout sensitivity. The number of capture probes (for example, the number of functionalized beads) can almost always be increased until sensitivity is limited by nonspecific binding rather than insufficient numbers of probes (Yelleswarapu V R et al., (2017), *Lab Chip* 17(6):1083-1094), but further improvement must come through careful optimization of washes and reactions. Protocol optimization are particularly challenging for multiplexed test development, since the optimal wash conditions (duration, ion content, surfactants, pH, and so on) are often different for different probe-analyte complexes.

A kinetic assay technology which measures the duration of individual binding events across a large sensor area as described herein addresses these limitations. In some of the embodiments the methods distinguish specific and nonspecific binding events without a single wash step. In some embodiments wash steps can be introduced to further improve specificity. Notably, kinetic analysis alleviates the need for a globally optimal wash protocol and therefore makes multiplexed tests straightforward.

'Solid-phase' surface sensors are sometimes criticized for having poor mass transport kinetics, as compared with bead-based assays. This effect can be alleviated by using a high flow rate, which makes the depletion layer very thin. For longer experiments or smaller sample volumes, peristaltic pumping and re-circulation can be used.

The unexpected bi-exponential histogram of dwell times suggested two different conformations of immobilized nanorods, each with different binding free energy: end-tethered and side-tethered.

Materials and Methods
Perfusion Chamber Assembly:

No. 1 coverslips 25.4 mm by 12.7 mm with a broadband antireflection coating on one side were purchased from Abrisa Technologies (Torrance, Calif.). Custom patterned silicon gaskets with were purchased from Grace Biolabs (Bend, Oreg.). Silicone gaskets were 25.4 mm by 12.7 mm, 0.15 mm thickness, with pressure-sensitive adhesive on one side. In preparation, gaskets were adhered to the non-coated side of the coverglass and stored with protective tape in place.

The perfusion chamber was assembled by aligning the gasket-window assembly to the IRIS chip, loading it into the clamp fixture, removing the protective tape and engaging the clamp to form seals between the chip and the gasket as well as with the sample inlet and outlet. The volume of the chamber was approximately 8 µL.

IRIS Digital Microarray Instrument for Dynamic Detection:

The operating principle of IRIS was previously described or included in references incorporated herein by reference. Briefly, the IRIS instrument consists of a reflectance microscope with a single high-powered LED for illumination (M660L4 LED with FB650-10 bandpass filter, Thorlabs) and a monochrome machine vision camera (Grasshopper GS3-U3-123S6M-C, Point Grey Research). The digital microarray implementation of IRIS is optimized for rapidly detecting individual gold nanorods based on their anisotropic light scattering properties. The design, optimization, and implementation of the optical system has been described in detail elsewhere (Sevenler D et al., (2018), *ACS Nano* 12(6):5880-5887). For dry IRIS chips, this system can detect single gold nanorods with a 10×, 0.3 NA objective. For dynamic experiments the system was entirely the same except that a 20×, 0.45 NA coverslip-corrected air immersion objective (Nikon CFI S Plan Fluor ELWD 20×) was used. The higher light collection efficiency compensated for the decreased intensity of nanorod light scattering due to immersion of the rods in water, and the collar allowed correction of spherical aberrations from the coverslip-air interface.

Assay Protocol:

The assay protocol was identical for all experiments, except that the concentration of the analyte was changed. First, the DNA-nanorod conjugates and synthetic DNA oligos were pre-mixed in a 'hybridization buffer' consisting of 10 mM phosphate pH 7.4, 600 mM Na+, 0.1% Tween-20, and 1 mM EDTA. 100 µL of nanorods stored at 140 pM were mixed with 900 µL of hybridization buffer containing the analyte ssDNA. The final nanorod concentration was 14 pM for all experiments. The mixture was vortexed briefly and sonicated for 10 seconds before storing at room temperature in a microcentrifuge tube. After 90 minutes, the sample was aspirated with a disposable 1 mL needle-tipped syringe. The needle tip was removed, and the syringe was connected to a Luer fitting on the end of the inlet tube. The outlet waste tube was left in conical vial. The syringe was mounted in a syringe pump and the sample was dispensed at 10 µL/min for up to 90 minutes. The instrument was re-focused as soon as the liquid sample filled the chamber. Video acquisition began 1-3 minutes after the sample first contacted the chip surface.

Image Acquisition:

Image acquisition was automated using the Micro-manager (Edelstein A D, et al. (2014), *J Biol Methods* 1(2). doi:10.14440/jbm.2014.36) microscope control software with custom scripts. Scripts have been made freely available online (www.github.com/derinsevenler/IRIS-API, accessed Apr. 19, 2019). Timepoints were taken every 30 seconds at each timepoint, a z-stack of nine images was acquired with a step size of two microns (i.e., a span of 16 microns). At each z-position, four images were acquired and averaged pixel-wise before saving to reduce shot noise.

Image Processing and Particle Detection:

The video data from each experiment consisted of an image hyperstack of 180 (t)×9 (z)×12.4 MP (x,y). A 86 µm by 86 µm (500 by 500 pixels) region of the video was cropped around each microarray spot. Nanorods in each region and timepoint were detected independently. The particle detection method described here is a refinement of methods described earlier (Sevenler D et al., MS (2018), *ACS Nano* 12(6):5880-5887; Trueb J T et al., (2017), *IEEE Journal of Selected Topics in Quantum Electronics* 23(2): 1-10) and has three steps: preprocessing, key point detection and key point filtering. First, a sparse pseudo-median filter is applied to each frame of the z-stack (made available online by others at (http://imagejdocu.tudor.lu/doku.php?id=plugin:filter:fast_filters:start, accessed Apr. 19, 2019) to estimate the image background. True median filtering is effective for removing punctate features but computationally expensive for larger kernels. The sparse pseudo-median algorithm was preferable due to its speed. Next, the normalized intensity image was calculated by pixelwise division of the original frame from the background. Finally, the 'normalized intensity range' (NIR) image was measured by projecting the maximum difference (i.e., max−min) at each pixel of the normalized intensity stack. Although not every nanorod is visible in every normalized intensity image in the stack, each particle is clearly visible in the resulting NIR image.

Key points in the NIR images were detected by applying a global threshold to binarize the image. Blobs in the binary image (i.e., regions brighter than the threshold) were enumerated and then filtered based on size and shape. Specifically, a minimum area, maximum area, and minimum area-perimeter ratio were specified. The detection threshold and key point filtering parameters were manually selected and then kept constant for all experiments IRIS Chip Fabrication:

150 mm polished silicon wafers with nominally 110 nm of thermally grown oxide were purchased from Silicon Valley Technologies (SVM, Santa Clara, Calif.). This film thickness was selected since it maximizes the visibility of nanorods with a longitudinal surface plasmon resonance peak at 650 nm (7). SVM also performed photolithography and oxide etching to pattern the chips with identifying features and dicing lines. Wafers were protected with a layer of photoresist before shipping to Patomac Laser (Baltimore, Md.) for through-hole drilling. Finally, the wafers were diced into 25.4 mm by 12.7 mm rectangular chips and stripped of photoresist at Boston University. Chips were inspected under the microscope to ensure cleanliness and stored in a sealed container.

Microarray Printing:

A 100 mm disposable plastic petri dish containing 10 mL of MCP-4 coating solution (Lucidant Inc, Sunnyvale Calif.) was prepared following manufacturer's instructions. IRIS chips were exposed to either pure oxygen or air plasma for five minutes to activate the surface with silanol groups. Chips were immediately submerged in the coating solution after plasma treatment and placed on an orbital shaker at room temperature for 30 minutes, during which the polymer covalently bonded to the glass via trimethoxysilane moieties. Chips were then washed thoroughly in DI water and dried in a vacuum oven at 80 C for 15 minutes. Chips were inspected under the microscope to ensure a clean, even coating and stored in a desiccator at room temperature for up to two weeks.

For microarray spotting, two vials containing one each of the amine-functionalized ssDNA surface probes selected for testing were prepared with a final concentration of 25 µM DNA, 150 mM phosphate pH 8.5. The high pH is required to facilitate reaction of the primary amines on the surface probes with N-hydroxysuccinimide moieties on the MCP-4 polymer. Single droplets of approximately 200 pL of the spotting solutions were printed onto the chip with a S3 Spotter (Scienion Inc, Berlin Germany) in a controlled humid chamber with 70% relative humidity. An interlocking pattern was used to reduce unused space on the array, such that each of the two conditions was printed in a square pattern with a pitch of 250 µm and offset by 125 µm horizontally and vertically from the other condition. Images taken by the spotter during printing were inspected to ensure droplets did not run together. The resulting spots were approximately 70-80 µm in diameter, with gaps of about 100 µm between them. Chips were left in the spotter overnight to maximize immobilization and washed thoroughly the next morning in saline-sodium citrate buffer (1×SSC) and DI water. After the final wash, chips were tipped nearly vertical and withdrawn slowly over the course of perhaps five seconds. This process uses surface tension to effectively dry the chip without evaporation, which helps maintain a clean surface.

Finally, the microarrays were incubated with so-called 'stabilizing' sequences. Previous work as well as our own experiments have shown that the presence of a double-stranded region on the surface probes accelerates hybridization ($k_{on}$). This is thought to reduce the conformational penalty to the binding free energy associated with the entropically unfavorable transition from flexible ssDNA to ordered and rigid dsDNA (in the case of displaced sequences), and/or allow additional base stacking interactions (in the case of adjacent non-displaced stabilizing region) (Prigodich A E et al., (2010), *J Am Chem Soc* 132(31):10638-10641; Galbiati S, et al. (2013), *PLoS ONE* 8(3):e59939). For these experiments, 12 base pair non-displacing stabilizing sequence was used, adjacent to the complementary region of the capture probes. Hybridization of the stabilizing sequences was performed at a concentration of 1 µM in 4×SSC buffer for 30 minutes at room temperature. Chips were washed four times in 1×SSC for 2 minutes each and dried by withdrawing at a steep angle from the final wash in the same manner as before. Chips were inspected under the microscope to ensure cleanliness and stored in a desiccator at room temperature for up to 2 months.

DNA-Gold Nanorod Conjugation:

The protocol for DNA-gold nanorod conjugation was optimized over time to resemble a hybrid of several methods described in literature (Hill H D et al., (2006), *Nat Protoc* 1(1):324-336; Zhang X et al., (2012), *J Am Chem Soc* 134(17):7266-7269; Hurst S J et al., (2006), *Anal Chem* 78(24):8313-8318). Citrate-capped nanorods with a longitudinal surface plasmon resonance peak at 650 nm and nominal dimensions 25 nm by 71 nm were used (Nanopartz Inc, Loveland, Colo., part number A12-25-650-CIT). Note that CTAB-stabilized nanorods should not be used directly with this protocol because they have a positive zeta potential, while citrate stabilized nanorods have a negative zeta potential.

First, 5 nmole of thiol-modified DNA probes (Table 1) were suspended in a solution of 170 mM phosphate buffer pH 8.0 with 100 mM dithiothreitol (DTT) for 3 hours at room temperature, to cleave the disulfide bonds and expose the active thiols. The probes were then desalted and eluted into DI water using an GE Healthcare illustra NAP-5 column using manufacturer's instructions. 6 mL of OD 1 nanorods (approximately 1 pmole) were transferred once in DI water by centrifugation (15 minutes @ 1,500 rcf) and then combined with the DNAs in a clean glass vial. The vial was protected from light with foil and placed on the orbital shaker. After 15 minutes, Tween-20 was added to a final concentration of 0.1% w/v. 30 minutes later, the solution was buffered to pH 3.0 with a final concentration of 10 mM citrate. The solution was rested for one hour, and then the sodium concentration was gradually increased to 200 mM via four additions of concentrated salt solution over the course of 24 hours. Salt additions were performed drop-bydrop while gently shaking the vial to avoid locally high concentrations. The vial was briefly sonicated and vortexed for 15 seconds each both before and after every salt addition. 2 hours after the last addition, the nanorods were washed five times in phosphate buffered saline solution with 1% Tween-20 (1×PBST) using the same speeds as before, to remove the excess unconjugated DNA. The final concentration of the conjugated nanorods was estimated based on visible light absorbance as compared to the stock solution of known concentration and adjusted to 140 pM for storage. Nanorods were stored at room temperature in an EPA vial with 1×PBST (phosphate buffered saline with 0.1% Tween-20) for up to 2 months.

What is claimed is:

1. A method for detecting at least one particle, the method comprising:
    providing a surface including a capture agent,
    providing a camera for generating an image of the surface,
    providing a computer, including a memory and a processor, connected to the camera;
    flowing a solution containing particles over the surface, thereby contacting the particles with the capture agent,
    collecting a plurality of sequential particle-images of the surface using the camera wherein each particle-image includes a time associated with it, and storing said particle-images in the memory,
    analyzing the plurality of particle-images using the processor to produce a catalog of particles based on a location of each particle in each particle-image and time associated data for each particle in the catalog, wherein the time associated data of each particle includes the time associated with each particle-image that includes the particle, and storing said catalog in the memory,
    eliminating a particle from the catalog in the memory if the time associated data of said particle does not span a time greater than a set time increment,
    outputting data from the catalog as the detection of the at least one particle.

2. The method of claim 1, further comprising combining a first particle and a second particle in the catalog, so that said combining identifies the first and second particle as a single particle in the catalog, if said first particle is listed in a first particle-image sequence in the catalog and then not listed in a subsequent second particle-image sequence of the catalog, and said second particle is listed in a third particle-image sequence of the catalog, and wherein the time spanned by the second particle-image sequence in the catalog corresponds to less than the set time increment, and wherein said combining includes assigning a time spanning the first particle-image sequence in the catalog, the second particle-image sequence in the catalog and the third particle-image sequence in the catalog to the first particle in the catalog.

3. The method as in claim 1, further comprising providing a user interface and outputting said data comprises providing catalog-representative data to the user interface.

4. The method of claim 3, wherein said catalog-representative data is in a form of a text data, image data, or graphed data.

5. The method of claim 1, wherein the surface is a component in an interferometric reflectance imaging sensor (IRIS) system comprising an objective lens for illuminating a detection region of a cartridge and collecting reflected light from the detection region, wherein the detection region includes the surface.

6. The method as in claim 1, wherein said capture agent is an antibody, a protein, a peptide an oligonucleotide, a complexing ligand, a single stranded DNA or RNA, a hapten, or a polymer.

7. The method as in claim 1, wherein said set time increment is between one second and one hour.

8. The method of claim 1, wherein said particles comprise a nanoparticle functionalized with a target, said capture agent having a high affinity for the target.

9. The method of claim 8, wherein the target is selected from the group consisting of a small molecule, a polymer, an antibody, a hapten, an oligonucleotide, a single stranded DNA or RNA, a protein and a peptide.

10. The method of claim 1, wherein the particle comprises a nanoparticle.

11. The method of claim 1, wherein the particle is a gold nano-particle.

12. The method of claim 1, wherein the particle is a virus.

* * * * *